United States Patent [19]
Torp et al.

[11] Patent Number: 6,099,471
[45] Date of Patent: Aug. 8, 2000

[54] METHOD AND APPARATUS FOR REAL-TIME CALCULATION AND DISPLAY OF STRAIN IN ULTRASOUND IMAGING

[75] Inventors: Hans Torp; Andreas Heimdal, both of Trondheim; Bjorn Olstad, Stathelle; Kjell Kristofferson, Oslo, all of Norway

[73] Assignee: General Electric Company, Milwaukee, Wis.

[21] Appl. No.: 09/167,896

[22] Filed: Oct. 7, 1998

Related U.S. Application Data

[60] Provisional application No. 60/061,291, Oct. 7, 1997.

[51] Int. Cl.$^7$ .................................................. A61B 8/00
[52] U.S. Cl. ........................... 600/438; 600/443; 600/440
[58] Field of Search .................................. 600/438, 440, 600/441–443, 454–456

[56] References Cited

U.S. PATENT DOCUMENTS

| | | | |
|---|---|---|---|
| 5,462,058 | 10/1995 | Yamada et al. | 600/454 |
| 5,615,680 | 4/1997 | Sano | 600/454 |
| 5,800,356 | 9/1998 | Criton et al. | 600/441 |

FOREIGN PATENT DOCUMENTS

WO 94/23652  10/1994  WIPO ............... A61B 8/12

OTHER PUBLICATIONS

Shapo, B.M. et al. "Ultrasonic Displacement and Strain Imaging of Coronary Arteries with a Catheter Array", IEEE OTS Symposium Proc. pp. 1511–1514 1995 Netscope [On-line ] [Retrieved on Dec. 8, 1999] Retrieved from Internet Site http://bul.eecs.umich.edu/crowj/publications.html.

Heimdal et al.: "Real–time Strain Velocity Imaging (SVI)" 1997 IEEE Ultrasonics Symposium Proceedings, vol. 2, 1997, pp. 1423–1426.

Jackson et al.: "3–D Ultrasonic Imaging of Structure and Elasticity of the Carotid Bifurcation" IEEE Ultrasonic Symposium Proceedings, vol. 2, 1995, pp. 1419–1422.

Kanai et al.: "Noninvasive Evaluation of local Myocardial Thickening and its Color–Coded Imaging" IEEE Transactions an Ultrasonics, Ferroelectrics and Frequency Control, vol. 44, No. 4, Jul. 1997, pp. 752–768.

Tsutsui et al.: "Comparative Usefulness of Myocardial Velocity Gradient in Detecting Ischemic Myocardium by a Dobutamine Challenge" J. Am. Coll. Cardiol., vol. 31, 1998, pp. 89–93.

McDicken et al.: "Colour Doppler Velocity Imaging of the Myocardium" Ultrasound in Med. & Biol., vol. 18, 1992, pp. 651–654.

Palka et al.: "Differences in Myocardial Velocity Gradient Measured Throughout the Cardiac Cycle in Patients With Hypertrophic Cardiomyopathy, Athletes and Patients With Left Ventricular Hyperthrophy Due to Hypertension" J. Am. Coll. Cardiol., vol. 30, 1997, pp. 760–768.

(List continued on next page.)

*Primary Examiner*—Francis J. Jaworski
*Attorney, Agent, or Firm*—McAndrews, Held & Malloy; Christian G. Cabou; Phyllis Y. Price

[57] ABSTRACT

An ultrasound system and method for calculation and display of strain velocity in real time is disclosed. Strain velocity may be determined from tissue velocity. Tissue velocity determined by measuring the pulse-to-pulse Doppler shift at range positions along an ultrasound beam and calculating tissue velocity based on the Doppler shift. The strain velocity is then calculated as a gradient of tissue velocity. Alternatively, linear regression methods may be used to calculate strain velocity from tissue velocity. Alternatively, strain velocity may be determined directly from the difference in Doppler shift between range positions. The result of the strain velocity determination may be displayed in a number of manners such as M-mode, color-coded video images or time-variation curves, and may be displayed in combination, or as a mixture, with a B-mode image. A reliability index may be calculated and used to modify the display of strain velocity information.

44 Claims, 3 Drawing Sheets

OTHER PUBLICATIONS

Nowicki, et al.: "Assessment of Wall Velocity Gradient Imaging Using a Test Phantom" Ultrasound in Medicine and Biology, vol. 22, 1996, pp. 1255–1260.

Uematsu, et al.: "Myocardial Velocity Gradient as a New Indicator of Regional Left Ventricular Contraction: Detection by a Two–Dimensional Tissue Doppler Imaging Technique" J. Am. Coll. Cardiol., vol. 26, 1995, pp. 217–223.

Fleming et al.: "Myocardial velocity gradients detected by Doppler imaging" The British Journal of Radiology, vol. 67, 1994, pp. 679–688.

Hartley et al.: "Doppler Measurement of Myocardial Thickening with a Single Epicardial Transducer" Am. J. Physiol., vol. 245, 1983, pp. H1066–H1072.

O'Donnel et al., "Internal Displacement and Strain Imaging Using Ultrasonic Speckle Tracking," IEEE Transactions on Ultrasonics, Ferroelectrics, and Frequency Control, vol. 41, No. 3, May 1994.

METHOD AND APPARATUS FOR REAL-TIME CALCULATION AND DISPLAY OF STRAIN IN ULTRASOUND IMAGING

CROSS-REFERENCE TO RELATED APPLICATIONS

Provisional Application Ser. No. 60/061,290, filed Oct. 7, 1997.

STATEMENT REGARDING FEDERALLY SPONSORED RESEARCH OR DEVELOPMENT

Not applicable.

BACKGROUND OF THE INVENTION

The present invention relates to diagnostic ultrasound systems which measure and image anatomical structures, and their movement. More particularly, the present invention relates to a signal processing method and apparatus for calculating and displaying of strain velocities, in localized parts of the image, to be used in ultrasonic imaging systems.

Recently, within the field of ultrasound imaging, physicians have become interested in using tissue strain and strain velocity for clinical measurements.

The term "strain" refers to a characteristic of material being examined. For example, the strain associated with muscle tissue corresponds to a ratio of the muscle tissues initial length and the change in muscle tissue length during a prescribed time interval. In ultrasound imaging, the rate of change of strain (e.g., strain rate, strain velocity, etc.) may be visually presented to a physician as a colorized 2-dimensional image, where variations in color correspond to different strain velocities. It has become apparent that the viability of a segment of the muscle is related to the amount of muscle strain and temporal behavior of the strain that is performed by, or is imposed on the muscle segment. Also, it has been determined that malignant tumors may be detected based on their resistance to compression.

One application of real-time strain velocity imaging is in cardiology. The strain velocity gives a direct and quantitative measure for the ability of the myocardium to contract and relax. By imaging along the myocard from an apical view, the local strain velocity component along the long axis of the heart can be measured. Measuring the local strain velocity component gives information about the local shortening and lengthening of the heart wall. By imaging from the parasternal view, the strain velocity component perpendicular to the heart wall can be found. Finding the strain velocity component perpendicular to the heart wall gives information about the local thickening of the muscle. Wall thickening measured with M-mode or from the 2D image is a commonly used measure for muscle viability. With strain velocity imaging, a direct measure for this thickening is available. The strain velocity images can potentially add to the diagnosis of a number of cardiac disorders including, for example:

Another application of strain velocity imaging is in heart transplants. Velocity variations inside the myocardium are important for the diagnosis of rejection after heart transplantation. The strain velocity images give a direct display of these velocity variations.

Another application of strain velocity imaging is in non-invasive electrophysiology. The preferred embodiment describes techniques to image the local contraction/relaxation contributions with a high spatial and temporal resolution. Local contraction/relaxation information can be used to accurately determine the localization of, for example, where the mechanical movement in the heart chambers is activated based on a cross section just below the AV-plane. Furthermore, abberent conduction pathways (Wolf-Parkinson-White) from the atrium to the ventricle can be localized for later ablation. Even the depth inside myocard of these paths can be better localized with this invention in order to determine if the patient should be treated with catheter techniques or surgical techniques.

Another application of strain velocity imaging is in measuring cardiac wall thickening. A well established methodology in cardiac diagnosis is to acquire a M-Mode image and to measure the wall thickening of myocardium during systole. The preferred embodiment provides techniques to take this wall thickening information and measure it in real-time with a high precision in both the spatial and temporal domain. The high diagnostic relevance of the current wall thickening measurements indicates that the imaging modality described in this invention contains highly relevant information for cardiac diagnosis.

To understand strain velocity in more detail, it is assumed that an object of initial length $L_0$ may be stretched or compressed or itself lengthens or contracts to a different length L. The one-dimensional strain, defined as $$\varepsilon = \frac{L - L_0}{L_0} \tag{1}$$

represents a dimensionless description of the change. If the length L is considered to be a function of time, and is described as $L(t)=r_1(t)-r_2(t)$, the temporal derivative of the strain, the strain velocity, can be found using the equation:

$$\dot{\varepsilon} = \frac{\partial \varepsilon}{\partial t} \tag{2}$$

If the velocity, v of every point in the object is known, an equivalent definition of the strain velocity is:

$$\dot{\varepsilon} = \frac{\partial v}{\partial r} \tag{3}$$

These equations also provide a useful description of the deformation of the object. In Eq. 3, r is the spatial direction of the stretching or compression. The relation between Eq. 2 and Eq. 3 can be seen if the length L is defined as $L(t)=r_2(t)-r_1(t)$, and $L_0=L(t_0)$, where $r_1$ is the distance to one end of the object, and $r_2$ is the distance to the other. As illustrated in Eq. 3, the strain velocity is in fact the spatial gradient of the velocity. The strain velocity thus measures the rate of the deformation of the object. If the strain velocity is zero, the shape of the object is not changing. If the strain velocity is positive, the length of the object is increasing, and if the strain velocity is negative, the length of the object is decreasing. Strain velocity is also known as rate-of-deformation, stretching, strain rate or velocity strain.

Strain imaging is currently an established research area in ultrasonic imaging. The degree of deformation in imaged structure may be estimated by correlation of 2D images obtained before and after a pressure increase. One disadvantage of estimating image deformation based on correlation of images is that the instantaneous value of the strain is not calculated nor displayed in real-time. The lack of a real-time capability is an important clinical disadvantage. For example, if strain imaging could be performed in real-time, strain imaging could be applied more effectively in cardiac ultrasound or could be used as an interactive inspection modality where anomalies in tissue compressibility can be visualized in real-time according to the pressure gradients that are applied to the imaged structures.

A method of position tracking has been proposed to estimate the local myocardial strain velocity based on radio frequency (RF) M-Mode acquisitions. The position tracking method is described in H. Kanai, H. Hasegawa, N. Chubachi, Y. Koiwa, and M. Tanaka, "Noninvasive evaluation of local myocardial thickening and its color-coded imaging," *IEEE Trans. on Ultrasonics, Ferroelectrics and Frequency Control*, vol. 44, pp. 752–768, 1997. However, the method described in the Kanai et al. article has the disadvantages of poor temporal resolution and high computational cost, which render real-time imaging difficult and costly. Furthermore, the method described in the Kanai et al. article is a manual M-mode technique, not well suited to form the basis for real-time two-dimensional strain images. Also, the strain velocity is a derivative of a velocity estimate and is therefore very noise sensitive. The fundamental velocity aliasing problem that is inherent in tissue velocity imaging makes noise difficult to overcome because aliasing prevents the pulse repetition frequency from being set at a low enough rate to allow a large observation time. If the observation time could be increased, the noise robustness of the strain velocity images could be significantly improved.

A need remains for an improved ultrasound system to overcome the above-identified difficulties. It is an object of the present invention to meet this need.

SUMMARY OF THE INVENTION

It is an object of the preferred embodiment of the present invention to provide an ultrasound system that is capable of calculating and displaying strain velocity.

It is a further object of the preferred embodiment to provide an ultrasound system that is capable of calculating and displaying strain velocity in real time.

It is a further object of the preferred embodiment to provide an ultrasound system that is capable of displaying strain velocity for a complete two-dimensional region.

It is another object of the preferred embodiment to provide an ultrasound system that displays strain velocity and yet overcomes the fundamental velocity aliasing problems that are inherent in tissue velocity imaging.

It is another object of the preferred embodiment to provide an ultrasound system that provides real-time imaging of strain velocity with high noise robustness.

It is another object of the preferred embodiment to provide an ultrasound system that provides real-time imaging of strain velocity with high temporal resolution.

It is another object of the preferred embodiment to provide an ultrasound system that provides real-time imaging of strain velocity in a computationally efficient and economical manner.

It is still another object of the preferred embodiment to provide an ultrasound system that displays strain velocity in a number of display formats.

These and other objects of the present invention are provided by an ultrasound system and method for calculation and display of strain velocity in real time. Velocity of each point of the image is determined by measuring the pulse-to-pulse Doppler shift at sample points along a scanline and calculating tissue velocity based on the Doppler shift. Strain velocity is then estimated as the gradient of the tissue velocity along the corresponding scanline. The tissue velocity gradient is estimated by measuring the velocity difference over a predefined distance, or by linear regression methods to estimate the slope of the velocity variation along the scanline.

A beam interleaving technique is used to lower the pulse repetition frequency (PRF) without reducing the total data acquisition time for the image. This allows accurate estimation of small velocity differences. However, a low PRF could cause frequency aliasing when the Doppler shift exceeds PRF/2, and thus give large errors in the velocity estimate.

One embodiment of the present invention provides a method to directly deduce the difference in Doppler shift between two points in the image, which is insensitive to the frequency aliasing effect. A significant improvement in the estimate of strain velocity is obtained without compromising a high frame-rate by deducing Doppler shift differences in a manner insensitive to frequency aliasing.

The result of the estimated strain velocity images are presented in the same way as for tissue velocity imaging: as a color-coded video images, as color-coded M-mode or as time-variation curves for single sample volumes. The color-coded images may be a mixture of the B-mode tissue image with the strain velocity image. The B-mode tissue image provides an anatomical reference for the detected anomalies in the strain velocity image.

Other objects, features, and advantages of the present invention will be apparent from the accompanying drawings and from the detailed description that follows below.

DETAILED DESCRIPTION OF THE PREFERRED EMBODIMENT

A method and apparatus are described for generating strain velocity measurements in real time. In the following description, numerous specific details are set forth in order to provide a thorough understanding of the preferred embodiment of the present invention. It will be apparent, however, to one of ordinary skill in the art that the present invention may be practiced without these specific details.

Figure 1:
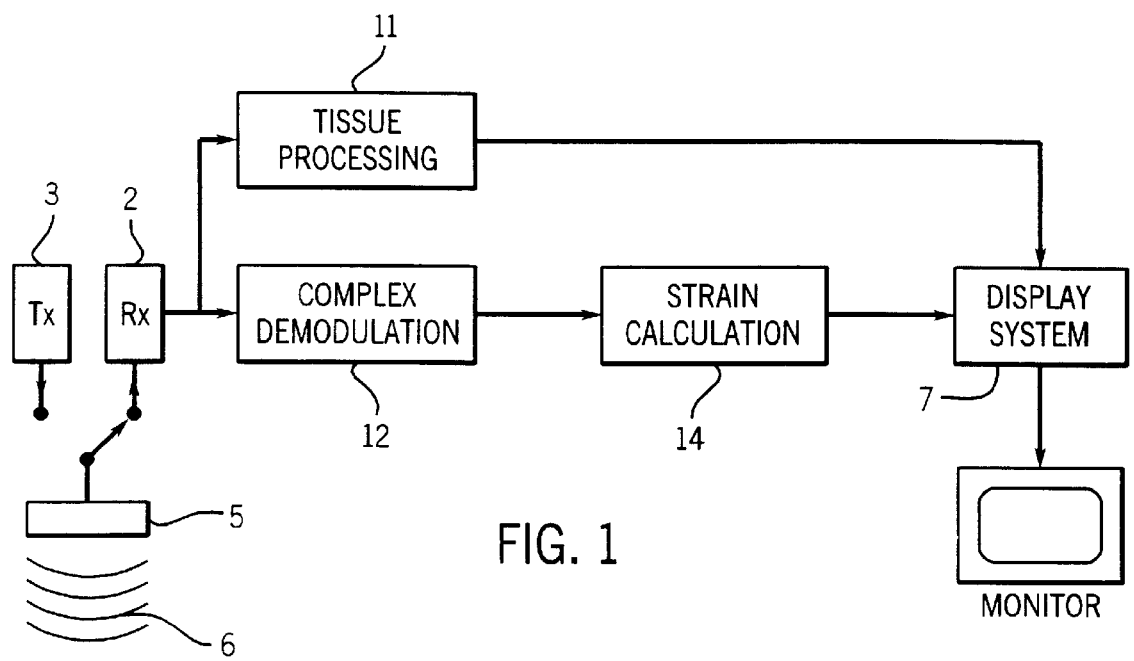
FIG. 1 illustrates an ultrasound system according to a preferred embodiment of the present invention.

A block diagram for an ultrasound imaging system according to a preferred embodiment of the present invention is shown in FIG. 1. An ultrasonic transducer 5 emits a pulsed ultrasonic beam 6 into the body. A transmitter 3 drives the transducer 5 to emit the pulsed ultrasonic beam 6. The ultrasonic pulses are backscattered from structures in the body, like muscular tissue, to produce echoes which return to and are detected by the transducer 5, see FIG. 1. A receiver 2 detects the echoes. The echoes are passed from a receiver 2 to a complex demodulation stage 12 and a tissue processing stage 11. The complex demodulation stage 12 demodulates the echo signals to form I, Q data pairs representative of echo signals.

The demodulated I, Q data pairs are complex Doppler signals that are passed to the strain calculation stage 14, which carries out strain velocity calculations as explained below. The complex Doppler signal is associated with a selected range in the area of interest of the color image. A complex Doppler signal typically comprises a segment of data samples which is used to estimate the Doppler shift. The echo signals are also passed to the tissue processing stage 11, which performs processing such as B-mode processing to form a 2D or 3D image of the anatomical structure scanned.

Next, the discussion turns to the techniques carried out by the strain calculation stage 14 to calculate strain velocity. The strain calculation stage 14 calculates the velocity SV(r) from an estimate of the tissue velocity v(r) in two points r and r+dr according to the following equation:

$$SV(r)=(v(r+dr)-v(r))/dr \quad (4)$$

The strain calculation stage 14 estimates the tissue velocity v(r) and v(r+dr) based on the demodulated complex Doppler signals for echo signals associated with the data points r and r+dr. The strain calculation stage 14 may utilize any of several known techniques to calculate the tissue velocities v(r) and v(r+dr). Alternatively, the strain calculation stage 14 may calculate the strain velocity SV(r), also referred to as the velocity gradient, based on a linear regression analysis of the estimated tissue velocities.

Alternatively, the strain calculation stage 14 calculates the strain velocity directly, without first calculating the tissue velocities. The strain velocity may be calculated directly based on the phase-variation of the complex correlation function, which is used in the "autocorrelation method", described below.

When calculating the strain velocity, the strain calculation stage 14 may utilize filtering techniques to obtain more robust estimates of the radial tissue velocity gradient. An example of such a filter is given in P. Saint-Marc, J. Chen, and G. Medioni. "Adaptive smoothing: A general tool for early vision" IEEE Trans. on Pattern Anal. and Machine Intell., 13(6), June 1991. The adaptive smoothing filters avoid erroneous velocity gradients between different structures like blood/tissue. The adaptive smoothing filters of the strain calculation stage 14 may also produce spatially piecewise constant strain velocity values. These properties of adaptive smoothing make the technique applicable for extensive spatial and temporal filtering in order to increase the robustness of the strain velocity value calculated by the strain calculation stage 14.

Next, an embodiment is described whereby the system utilizes autocorrelation to estimate tissue velocities. Optionally, the correlation function may be averaged in space with neighboring ranges and/or vectors, to reduce estimation variance. The Doppler shift is then calculated from the angle of the averaged correlation function.

The correlation function used to calculate Doppler shift may be calculated by any of several known functions. For instance, an autocorrelation method for ultrasound blood flow velocity measurements can be found in C. Kasai, K. Namekawa, A. Koyano, and R. Omoto, "Real-Time Two-Dimensional Blood Flow Imaging Using an Autocorrelation Technique" IEEE Trans. Sonics Ultras., vol. SU-32. pp. 458–464 (1985). Another autocorrelation method for tissue velocity imaging is described in W. N. McDicken, G. R. Sutherland, and C. M. Moran, "Color Doppler velocity imaging of the myocardium," Ultrasound Med. Biol., vol. 18, nos 6/7, pp. 651–654, (1992).

In more detail, the velocity v can be calculated by first obtaining the pulse-to-pulse correlation function from the complex Doppler signal packet x(r,t); t=1, ... ,N.

$$P(r) = \sum_t conj(x(r,t))x(r,t); \quad (5)$$

$$R(r) = \sum_t conj(x(r,t))x(r,t+1);$$

where conj( ) means complex conjugate. In equation (5) the formula for the Doppler signal power P, as well as the complex autocorrelation R are given.

Optionally, before performing the correlation operation, the strain calculation stage 14 may subject the complex Doppler signal to clutter suppression, such as a regression wall filter. The purpose of the wall filter is to suppress signals from acoustical noise, which often have a lower Doppler shift than the signals from the measured object. It is preferable to avoid systematic errors in the velocity estimate, which may occur with filters of this form. These problems are discussed in H. Torp, "Clutter rejection filters in Color Flow Imaging: A theoretical Approach," IEEE Trans. on Ultrasound, Ferroelectrics, and Frequency control, vol. 44, 1997. The degree of clutter suppression may be adjustable, and in some situations, when the acoustical noise level is low, the clutter filter may be omitted.

The velocity is obtained from the phase angle of R:

$$v(r)=c/2\int o\, phase(R(r))/2\pi T \quad (6)$$

where c=speed of sound, and T is the time between the consecutive pulses. Once the velocity v(r) is calculated, the foregoing correlation function is repeated for velocity v(r+dr), where dr is an incremental distance which is a parameter of the estimation algorithm. An increased value of dr may give a decreased spatial resolution, but improve the accuracy of the strain velocity estimate. Next, the strain velocity SV(r) is calculated according to equation (4) above.

It is preferable that, when using a correlation function, the velocity not exceed the Nyquist limit. This occurs when the velocity magnitude exceeds the Nyquist Velocity limit, corresponding to phase(R)=π

$$Vnyqyuist=c/(4*fo*T)=c*PRF/(4fo) \quad (7)$$

Figure 2:
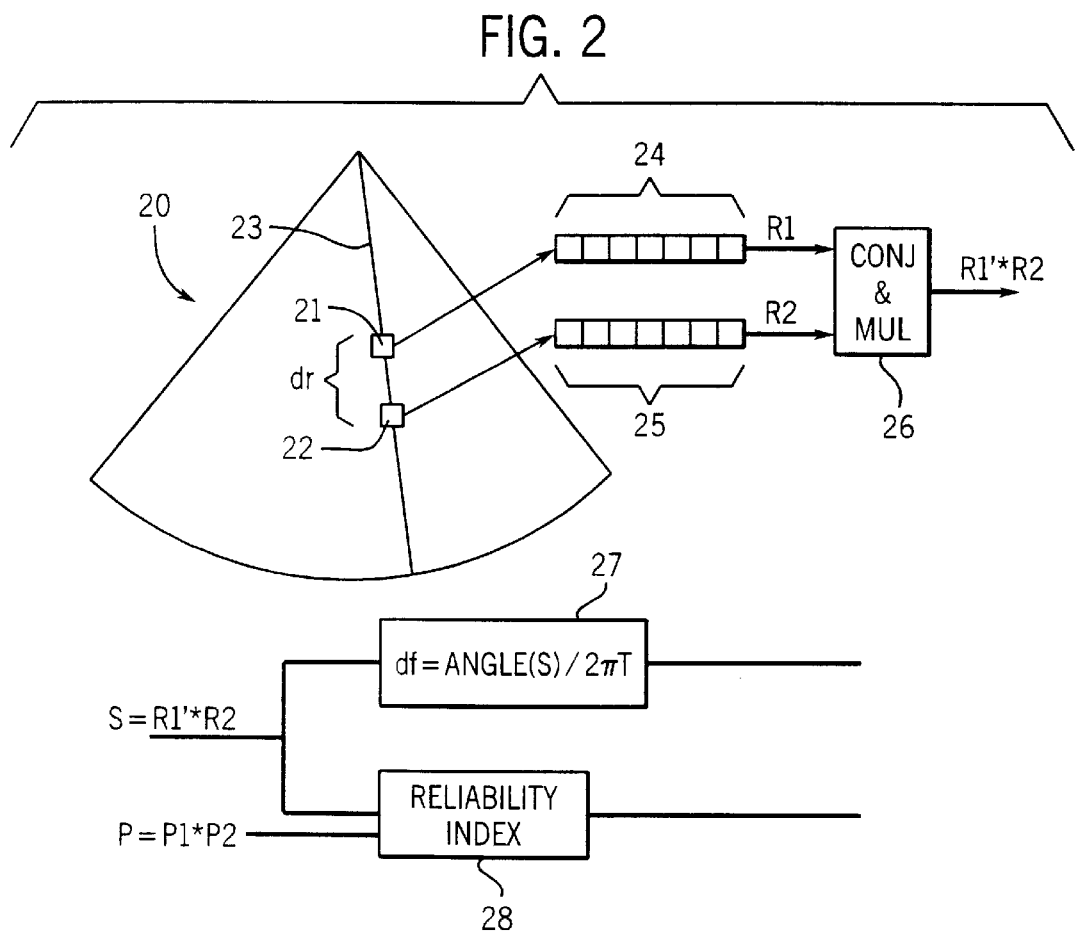
FIG. 2 illustrates exemplary signal packets x1 and x2 from two range positions along a scanline according to a preferred embodiment of the present invention.

Next, an alternative embodiment is described, in connection with FIG. 2 whereby the strain calculation stage 14 directly measures the strain velocity. The strain velocity can be found directly from the phase difference between correlation values at two different points in the image separated by a distance dr, see FIG. 2. The correlation values R1=R(r) and R2=R(r+dr) are calculated by the strain calculation stage 14 using equation (5). The receiver 2 records at least two continuous echo signals for the corresponding regions within the two range positions 21 and 22. The complex demodulator 12 converts the echo signals to signal packets 24 and 25 of data samples. The strain calculation stage 14 calculates complex correlation functions R1 and R2, and powers P1 and P2 from the packets 24 and 25. The strain calculation stage 14 includes an arithmetic module 26 which calculates strain correlation S. Then the complex product between R2 and conjugate of R1 is formed. The resulting complex number S will then have a phase angle equal to the difference between the phase angle of R2 and R1

$$S(r)=conj(R(r))*R(r+dr) \quad (8)$$

The "Strain correlation function" S(r) may also be averaged both in the beam direction, and between neighboring beams, to reduce estimation variance.

FIG. 2 shows a sector scan 20 containing two range positions 21 and 22 along a scanline 23. The "strain correlation" S is calculated as S=conj(R1)*R2, the angle of S is proportional to the difference in Doppler shift between range positions 21 and 22.

The strain calculation stage 14 also includes a strain velocity module 27 and a reliability index module 28. The strain calculation module 27 uses the following expression to calculate the strain velocity SV(r) from the strain correlation function:

$$SV(r)=c/(4\pi drTfo) \text{ phase } (S(r)) \qquad (9)$$

Usually, the velocity difference v(r+dr)−v(r) is much lower than each individual velocity. Therefore, the Nyquist strain limit, which occurs when phase(S)=π

$$SVnyquist=Vnyquist/dr \qquad (10)$$

is much less likely attained.

The advantage of using the direct method for strain velocity measurement is apparent in the following typical example for cardiac application: Maximum cardiac muscle velocity is typically 0.1 m/s, and max strain velocity is 2.0 (m/s)/m. With fo=4 MHz, the PRF should be at least 1 kHz to avoid velocity aliasing. If dr=8 mm, minimum PRF to avoid strain velocity aliasing is 160 Hz. By lowering the PRF with a factor 6, a similar decrease in estimation error can be obtained.

Figure 3A:
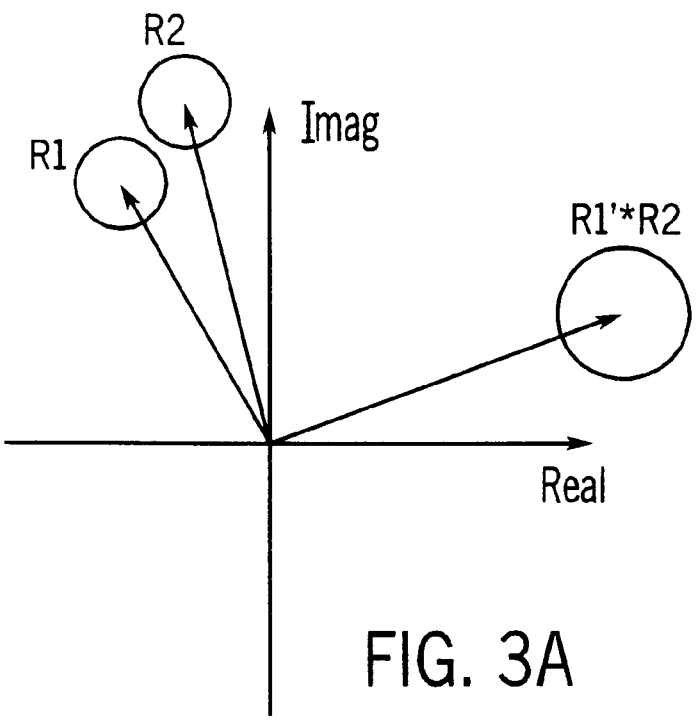
FIGS. 3a and 3b illustrates correlation values R1 and R2 in the complex plane, for two different pulse repetition frequencies (PRFs).
Figure 3B:
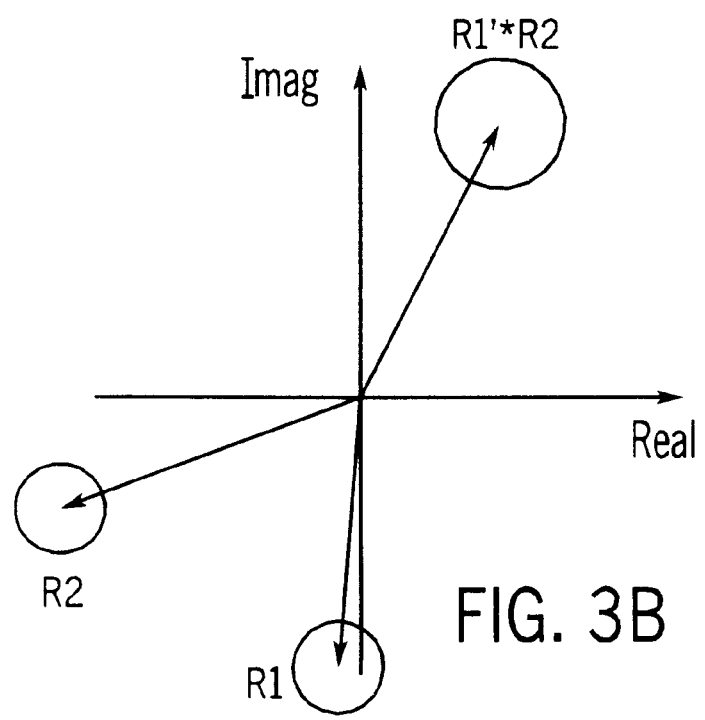

In FIGS. 3A and 3B, the effect of decreasing the PRF is illustrated. FIGS. 3A and 3B show the correlation values R1 and R2 in the complex plane, for two different PRF's. The circles indicate the random fluctuations of R1 and R2 around the true value. In FIG. 3B, the PRF is lowered by a factor 2. The angle of R1 and R2 will then increase by a factor 2, and aliasing error will occur (i.e., because phase(R)>π). However, the angle difference will still give the correct Doppler shift difference (i.e., because phase(S)<π), and the random error in the SV estimate will decrease.

In parts of the image, more chaotic movement may occur, which makes strain velocity difficult to measure. The reliability index module 28 corrects for chaotic movement by calculating an index indicating the reliability of the strain velocity calculation.

The reliability index module may use the following reliability index ri(r):

$$ri(r)=abs(S(r))/(P(r)*P(r+dr)) \qquad (11)$$

The reliability index is compared with a threshold, to remove noisy SV-values from the display. The reliability index may also be used to modulate (or modify) the color scale used to display the strain velocity, for instance, by decreasing the saturation of the color when the ri—value is low.

The preferred embodiments of the present invention may be implemented in a system that employs a beam-interleaving. Velocity imaging requires two or more pulses in the same beam direction to be able to measure the velocity. The result is a packet of signal samples in each range point along the beam, and the packet size N equals the number of pulses. Thus, N>=2. This signal packet (after complex demodulation) is the Doppler signal. The time between the pulses is referred to as the pulse repetition time, and its inverse, the pulse repetition frequency (PRF). The total observation time for the moving objects is then N/PRF. Generally, the velocity estimation error decreases when the observation time increases. This can be achieved either by increasing the packet size, or decreasing the PRF. In both cases, the acquisition time, and the frame-rate is reduced. Beam interleaving is a technique where M pulses (interleave-size) are sent sequentially in different beam directions in N cycles. In this way, the PRF is lowered by a factor M, without increasing the total acquisition time for the image, and thus keeping the frame-rate constant, independent of PRF.

The most extreme situation occurs when the interleave size M equals the number of beams in the image. In this case, the packet size can be set to N=1, and the Doppler signal can be obtained by picking one signal sample from each frame in the real-time sequence of frames. Then the PRF equals the frame rate, and a continuous stream of Doppler signals samples is available for analysis in each point in the image. The calculation of strain can then be performed on a "time-sliding" signal packet of arbitrary length, and with arbitrary degree of overlap between the signal packets.

The preferred embodiments of the present invention may be implemented in a system that offers B-mode imaging. Separate pulses can be used to generate the B-mode tissue image to obtain a tissue image with higher resolution than the tissue velocity image or strain velocity image, i.e. short pulse and high number of scanlines.

Alternatively, however, the B-mode image may be obtained from the same pulses as the strain velocity image. For low PRF requirement, the correlation can be performed frame-to-frame. The equivalent PRF will then be equal to the frame-rate. The frame-rate can be further increased by applying "multi-line acquisition" (MLA). This technique allows reception of more than one receiver beam for each transmitted pulse. Typically, a slightly broader ultrasonic beam is transmitted, and the receiver beam-former is set up to receive and separate the signals from 2 or more different beam direction within the transmit beam opening angle. In this way, an increase in frame rate can be obtained by limiting the number of transmit beam directions.

The preferred embodiments of the present invention may be implemented in a system that offers harmonic imaging. Harmonic imaging, (or octave imaging) where the second harmonic frequency of the transmitted signal frequency is used for display, has been shown to reduce noise artifacts in B-mode images. This technique can be combined with the preferred embodiments of the present invention in three ways: first by using the harmonic B-mode tissue image in combination with the strain image as described above, second, by using the harmonic part of the received signal as a basis for the strain velocity calculation or third, by combining these first and second ways.

Intravascular imaging has so far been mainly limited to tissue imaging. The application of tissue velocity imaging in intravascular imaging can provide information about the movement of the vessel wall relative to a catheter.

Figure 4:
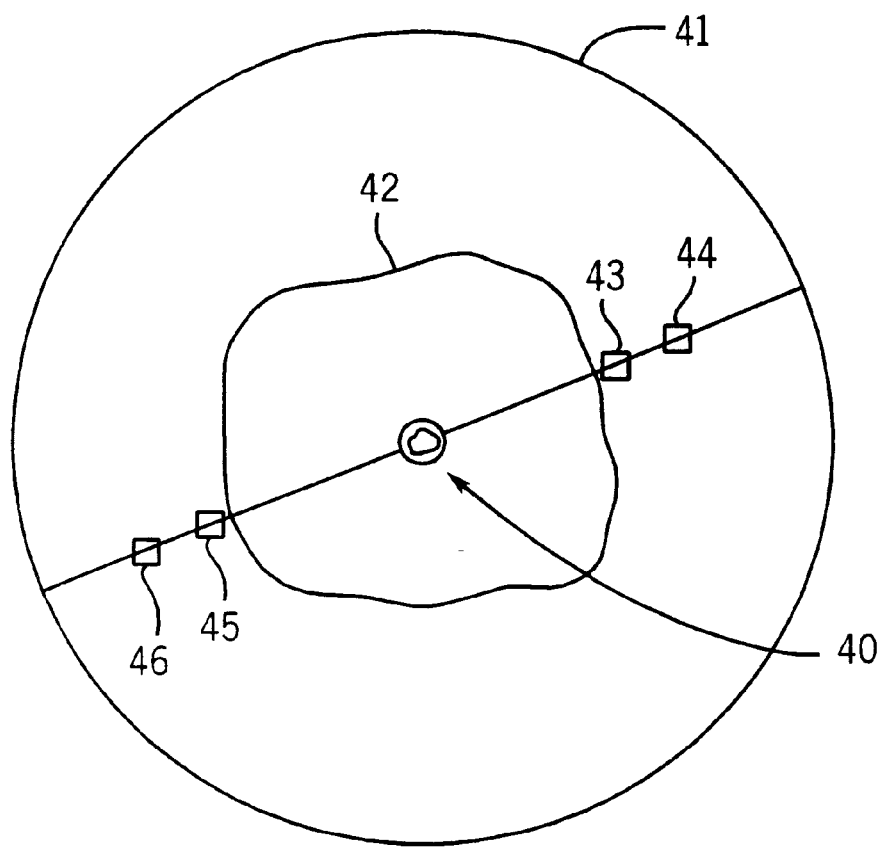
FIG. 4 illustrates an example of an intravascular ultrasound image created by a preferred embodiment of the present invention.

FIG. 4 shows an example of an intravascular ultrasound image. The catheter 40 usually acquires a circular image 41. Inside the image there will be an interface 42 between the vessel lumen and the vessel wall. The sample points 43 and 44 correspond with points 21 and 22 in FIG. 2. Similarly, the sample points 45 and 46 correspond with points 21 and 22 in FIG. 2. The radial motion of a given sample point like 43 relative to the catheter 40 can be accurately measured by tissue velocity imaging. Furthermore, the location of the sample point 43 can be tracked radially as a function of time if the sample volume is repositioned according to the measured velocity multiplied with the time delay between consecutive image frames. If this is repeated for two points diametrically positioned on the vessel wall (43 and 45), one can make very sensitive estimates of the variations in vessel diameter. Similarly, variations in the vessel area can be monitored if the above analysis is repeated for all radial directions. The variations in vessel diameter/area can be used alone or together with auxiliary information like pressure to estimate important physiological parameters of the vessel. The strain velocity imaging described in this patent can be used to image the compressibility of the vessel wall. This can potentially be very important in the differentiation between various types of soft and hard plaque.

Strain velocity imaging can also be performed on soft parts of the body by applying an increasing pressure on the probe against the skin. The tissue will then be compressed, but hard regions will be compressed less than soft regions. This difference will show up in the strain velocity image. This type of imaging can for instance be performed when looking for tumors in the breast, the prostate, the thyroid or the liver, since tumors often are less compressible than normal tissue.

In the foregoing specification the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarding in an illustrative rather than restrictive sense.

What is claimed is:

1. A method for providing real-time strain velocity images of a spatial region comprising:

firing ultrasound pulses into an area of interest of the spatial region;

acquiring echo signals for a plurality of range positions along ultrasonic beams in an area of interest using a beam interleaving technique to acquire echo information along different beam directions during a time interval between two consecutive ultrasound pulse firings in a common direction;

estimating, in real-time, strain velocities from said acquired echo signals for said range positions inside said spatial region; and displaying estimated strain velocities for each range position at spatial coordinates on a display unit associated with said spatial region to provide a real-time image of said strain velocities for said spatial region.

2. The method according to claim 1, wherein the step of estimating strain velocities comprises:

estimating tissue velocity for range positions along the ultrasonic beam based on the echo signals; and calculating the strain velocity as a spatial derivative of the tissue velocity.

3. The method according to claim 2 wherein the spatial derivative is found with a linear regression of the tissue velocity for range positions along the ultrasonic beam.

4. The method according to claim 3, wherein the step of estimating strain velocities comprises:

estimating tissue velocity for range positions along the ultrasonic beam based on the echo signals; and calculating the strain velocity by determining a velocity difference between estimated tissue velocities associated with at least a first and second range positions and dividing the velocity difference by a distance between the first and second range positions.

5. The method according to claim 1, wherein the step of estimating the strain velocity comprises:

estimating a complex pulse-to-pulse correlation $R(r)$ for a number of range positions along the ultrasonic beam based on the echo signals;

determining a strain correlation function, $S(r)$, over a radial distance $dr$ according to an equation $S(r)=\text{conj}(R(r))*R(r+dr)$; and calculating the strain velocity according to an equation $SV(r)=c/(4\pi dr Tfo)\ \text{phase}\ (S(r))$.

6. The method according to claim 1, wherein the step of estimating the strain velocity comprises:

estimating a complex pulse-to-pulse correlation for a number of range positions along the ultrasonic beam, based on the echo signals;

calculating a strain correlation function from at least two range positions separated by a given radial distance; and calculating the strain velocity based on the phase of the strain correlation function.

7. The method according to claim 6 wherein the strain correlation function is given by multiplying the conjugate of the complex pulse-to-pulse correlation for a first range position by the complex pulse-to-pulse correlation for a second range position where said second range position is located the given radial distance from said first range position.

8. The method according to claim 7 wherein the strain velocity is given by dividing a numerator defined as the product of the phase angle of the strain correlation function and the speed of sound by a denominator defined as the product of 4, $\pi$, the given radial distance, the ultrasound frequency and the time between consecutive pulses of said multiple of pulses.

9. The method according to claim 6 further comprising the step of temporally averaging the strain correlation function before calculating the strain velocity.

10. The method according to claim 6 further comprising the step of spatially averaging the strain correlation function before calculating the strain velocity.

11. The method according to claim 1 wherein the step of displaying the estimated strain velocity comprises combining a B-mode tissue image and the strain velocities at corresponding spatial coordinates in a color encoding.

12. The method according to claim 1 wherein the step of displaying the estimated strain velocity comprises combining an M-mode tissue image and the strain velocities at corresponding spatial coordinates in a color encoding.

13. The method according to claims 1 wherein the step of displaying the estimated strain velocities includes displaying the estimated strain velocity for a complete two-dimensional region.

14. The method according to claim 1 wherein the estimated strain velocities are estimated for a three-dimensional region and displayed with a three-dimensional visualization technique.

15. The method according to claim 1 wherein multiple line acquisition techniques are applied to further increase the resulting frame-rate.

16. The method according to claim 1 further comprising the steps of:

calculating a strain reliability index as a function of signal power for each sample point inside the said spatial region; and modifying the display of the strain velocity according to the strain reliability index.

17. The method according to claim 1 wherein the strain reliability index given by dividing the absolute value of the product of the conjugate of the complex pulse-to-pulse correlation for a first range position and the complex pulse-to-pulse correlation for a second range position by the signal power at one of said first or second range positions.

18. The method according to claim 1 wherein a harmonic of the echo signals is used to estimate the strain velocities.

19. The method according to claim 1 wherein the strain velocity images are generated simultaneously with the application of an external force to produce a pressure gradient in the spatial region.

20. The method according to claim 1 wherein the strain velocity images are generated while simultaneously applying changing pressure against the imaged spatial region.

21. The method according to claim 1 wherein the echo signals are acquired using intravascular ultrasound techniques to assess regional changes in the vessel wall properties.

22. A method for generating real-time strain velocity images comprising:

acquiring harmonic signals for echo signals received from a plurality of range positions along an ultrasonic beam in an area of interest to cover a spatial region;

estimating in real-time strain velocities for said range positions inside said spatial region based on the harmonic signals for the acquired echo signals; and displaying estimated strain velocities for each range position at spatial coordinates on a display unit associated with said spatial region to provide a real-time image of said strain velocities for said spatial region.

23. The method according to claim 22, wherein the step of estimating strain velocities comprises:

estimating tissue velocity for range positions along the ultrasonic beam based on the echo signals; and calculating the strain velocity as a spatial derivative of the tissue velocity.

24. The method according to claim 23 wherein the spatial derivative is found with a linear regression of the tissue velocity for range positions along the ultrasonic beam.

25. The method according to claim 22, wherein the step of estimating strain velocities comprises:

estimating tissue velocity for range positions along the ultrasonic beam based on the echo signals; and calculating the strain velocity by determining a velocity difference between estimated tissue velocities associated with at least a first and second range positions and dividing the velocity difference by a distance between the first and second range positions.

26. The method according to claim 22, wherein the step of estimating the strain velocity comprises:

estimating a complex pulse-to-pulse correlation R(r) for a number of range positions along the ultrasonic beam based on the echo signals;

determining a strain correlation function, S(r), over a radial distance dr according to an equation S(r)=conj(R(r))*R(r+dr); and calculating the strain velocity according to an equation SV(r)=c/(4πdrTfo) phase (S(r)).

27. The method according to claim 22, wherein the step of estimating the strain velocity comprises:

estimating a complex pulse-to-pulse correlation for a number of range positions along the ultrasonic beam, based on the echo signals;

calculating a strain correlation function from at least two range positions separated by a given radial distance; and calculating the strain velocity based on the phase of the strain correlation function.

28. The method according to claim 27 wherein the strain correlation function is given by multiplying the conjugate of the complex pulse-to-pulse correlation for a first range position by the complex pulse-to-pulse correlation for a second range position where said second range position is located the given radial distance from said first range position.

29. The method according to claim 28 wherein the strain velocity is given by dividing a numerator defined as the product of the phase angle of the strain correlation function and the speed of sound by a denominator defined as the product of 4, π, the given radial distance, the ultrasound frequency and the time between consecutive pulses of said multiple of pulses.

30. The method according to claim 27 further comprising the step of temporally averaging the strain correlation function before calculating the strain velocity.

31. The method according to claim 27 further comprising the step of spatially averaging the strain correlation function before calculating the strain velocity.

32. The method according to claim 22 wherein the step of displaying the estimated strain velocity comprises combining a B-mode tissue image and the strain velocities at corresponding spatial coordinates in a color encoding.

33. The method according to claim 22 wherein the step of displaying the estimated strain velocity comprises combining the M-mode tissue image and the strain velocities at corresponding spatial coordinates in a color encoding.

34. The method according to claims 22 wherein the step of displaying the estimated strain velocities includes displaying the estimated strain velocity for a complete two-dimensional region.

35. The method according to claim 22 wherein the estimated strain velocities are estimated for a three-dimensional region and displayed with a three-dimensional visualization technique.

36. The method according to claim 22 wherein said spatial region is limited to a single point and the strain velocities are displayed as a spectral or strain velocity curve versus time.

37. The method according to claim 22 wherein a said acquiring echo signals is performed with a low pulse repetition frequency.

38. The method according to claim 37 wherein said low pulse repetition frequency is combined with a beam interleaving technique for increasing the frame-rate by acquiring information from different beam directions in the time interval between two consecutive pulses in a given direction.

39. The method according to claim 38 wherein multiple line acquisition techniques are applied to further increase the resulting frame-rate.

40. The method according to claim 22 further comprising the steps of:

calculating a strain reliability index as a function of signal power for each sample point inside the said spatial region; and modifying the display of the strain velocity according to the strain reliability index.

41. The method according to claim 40 wherein the strain reliability index given by dividing the absolute value of the product of the conjugate of the complex pulse-to-pulse correlation for a first range position and the complex pulse-to-pulse correlation for a second range position by the signal power at one of said first or second range positions.

42. The method according to claim 22 wherein the strain velocity images are generated simultaneously with the application of an external means to produce a pressure gradient in the spatial region.

43. The method according to claim 22 wherein the strain velocity images are generated while simultaneously applying changing pressure against the imaged spatial region.

44. The method according to claim 22 wherein the echo signals are acquired using intravascular ultrasound techniques to assess regional changes in the vessel wall properties.

* * * * *